United States Patent
Peck et al.

[11] Patent Number: 6,094,627
[45] Date of Patent: Jul. 25, 2000

[54] HIGH-PERFORMANCE DIGITAL SIGNAL AVERAGER

[75] Inventors: Jeffrey V. Peck, Knoxville; Dale A. Gedcke, Oak Ridge; Russell D. Bingham, Knoxville, all of Tenn.

[73] Assignee: PerkinElmer Instruments, Inc., Wellesley, Mass.

[21] Appl. No.: 09/072,388

[22] Filed: May 4, 1998

Related U.S. Application Data

[60] Provisional application No. 60/048,311, May 30, 1997.

[51] Int. Cl.[7] ............................... H03M 1/00; H03M 1/20
[52] U.S. Cl. ............................ 702/199; 341/61; 341/155; 702/194
[58] Field of Search ..................................... 702/199, 194, 702/146; 701/115, 102, 112; 341/131, 61, 118, 120, 144, 155, 141, 143; 708/313

[56] References Cited

U.S. PATENT DOCUMENTS

| | | |
|---|---|---|
| 3,639,741 | 2/1972 | Carrick ..................................... 341/132 |
| 4,472,631 | 9/1984 | Enke et al. ............................... 250/281 |
| 4,490,806 | 12/1984 | Enke et al. ............................... 708/445 |
| 4,642,778 | 2/1987 | Hieftje et al. ............................. 702/23 |
| 5,175,430 | 12/1992 | Enke et al. ............................... 250/282 |
| 5,227,794 | 7/1993 | Whikehart ............................... 341/141 |
| 5,367,162 | 11/1994 | Holland et al. ......................... 250/287 |
| 5,428,357 | 6/1995 | Haab et al. .............................. 341/155 |
| 5,453,613 | 9/1995 | Gray et al. .............................. 341/155 |
| 6,028,543 | 2/2000 | Gedcke et al. .......................... 341/131 |

*Primary Examiner*—Kamini Shah
*Attorney, Agent, or Firm*—Pitts & Brittian, P.C.

[57] ABSTRACT

A digital signal averager for averaging data collected by an analog detector is provided. The digital signal averager includes an analog-to-digital converter for converting the analog detector output to a digital signal for processing, a timing device for generating delayed timing pulses for sequencing operation of the digital signal averager, an averaging device for summing and storing data. The delayed timing pulses allow data to be acquired by the ADC at a series of variably offset timing sequences relative to a trigger pulse. Offsetting the data acquisition timing sequences by time slices smaller than the actual sample rate of the ADC allows data to be acquired at a higher effective sampling rate. One complete series of offset timing sequences provides a data set containing all the information which would be acquired by a ADC having a faster sampling rate. Accuracy of the data is further enhanced by a series of parallel averaging devices, including one processing device and multiple memory devices, which perform real-time averaging of data. A digital signal processor applies a method for data compression to the averaged data to reduce data transfer rate and storage capacity requirement for transferring the averaged data to an analysis and storage device for long-term storage.

12 Claims, 5 Drawing Sheets

HIGH-PERFORMANCE DIGITAL SIGNAL AVERAGER

This application claims the benefit of U.S. Provisional Application Ser. No. 60/048311, filed May 30, 1997.

TECHNICAL FIELD

This invention relates to the field of digital signal averaging. More specifically it relates to a high-performance digital signal averaging system adapted for use with a combined chromatography, time-of-flight mass spectrometry instrument.

BACKGROUND ART

Determination of the composition of samples containing very large molecules is important in many areas of chemistry and biology. Researchers regularly combine gas, liquid, or capillary electrophoresis chromatography with time-of-flight mass spectrometry (C/TOF-MS) to identify and obtain information about the internal structure of the molecules. The chromatography device separates a sample, most commonly, by molecular weight, though those skilled in the art recognize that other physical, chemical or ionic characteristics can also be used to separate the sample. Further, the chromatography device elutes a semi-continuous stream of molecules, with lighter molecules generally eluted first, then gradually heavier ones. This molecular stream is fed directly into a time-of-flight mass spectrometer (TOF-MS) system. In a TOF-MS, the controls for the ionization and fragmentation chamber can be adjusted to inject the unfragmented molecules or to fragment the molecules upon injection into the TOF-MS system. The purpose of the TOF-MS system is to continuously measure the masses of the injected molecules or fragments in order to identify the molecules as they elute from the chromatograph.

Once in the TOF-MS system, the molecules or molecular fragments undergo ionization and are accelerated toward an ion detector by a high voltage pulse. The TOF-MS system determines the mass of the molecules or molecular fragments by measuring the time required for the accelerated ions to travel the fixed distance of the TOF-MS chamber. Ions with the lowest mass and highest electrical charge arrive first at the detector with heavier ions arriving later in time. The time required for the slowest molecule or fragment to travel the entire distance is one detection cycle, also referred to as one record, of the TOF-MS system. In order to improve the accuracy of the measurement, multiple records are acquired in rapid succession and added together to form a mass spectrum. The time required to measure one mass spectrum from a single molecular type eluted from the chromatography device is one "chromatograph sampling interval" of the TOF-MS system. The resulting mass spectrum from the TOF-MS system gives a "fingerprint" which can be used for purposes of identification and structural analysis of the molecules.

In general, there are two popular alternatives for converting the analog signal from the ion detector to a digital record: a) a time digitizer or b) a transient digitizer. With a time digitizer, the ion arrival rate must be limited to a low value so that the time digitizer can measure the arrival time of each ion and convert that time to a digital number. A time digitizer can yield very precise time measurements, but cannot accommodate the very high ion arrival rates required for high sensitivity in a C/TOF-MS instrument.

With a transient digitizer the ion rates can be increased so that many ions of the same mass-to-charge ratio (m/z) arrive at the ion detector simultaneously. The result is an analog voltage pulse whose amplitude is approximately proportional to the number of ions in the pulse. In the transient digitizer, an ADC samples the output waveform of the ion detector and converts the measured analog voltage to a digital representation. The ADC sampling is driven by the edges of a clock pulse so that the detector voltage is sampled periodically. For example, the range of ion flight times from zero to 131 microseconds is typically sampled at two nanosecond intervals. The digital representations of the voltage samples are sequentially stored in a digital memory to form a single record.

Due to the variability caused by ion statistics and the statistics governing the signal gain in the ion detector, one record does not provide an adequate signal-to-noise ratio. Consequently, multiple records must be acquired and summed in rapid succession. A transient digitizer which can perform this rapid summing is known as a digital signal averager.

Although a digital signal averager can process much higher ion rates than a time digitizer, it suffers from worse time resolution. Consequently, this invention focuses on improving the time resolution of the digital signal averager while achieving exceptionally high rates of data collection. For example using the methods disclosed in the present invention, the digital signal averager can acquire and store TOF-MS spectra at a sustained rate of at least 10 spectra per second for a period of at least thirty minutes. Each spectrum in the example is the sum of 189 records and spans flight times from zero to 131 microseconds with data points sampled at 0.5 nanosecond intervals.

Other digital signal averaging devices have been previously disclosed. Typical of the art are those devices disclosed in the following U.S. Patents:

| Pat. No. | Inventor(s) | Issue Date |
|---|---|---|
| 5,428,357 | Haab et al. | Jun. 27, 1995 |
| 4,490,806 | Enke et al. | Dec. 25, 1984 |

The U.S. Pat. No. 5,428,357 patent discloses a high speed data acquisition system and method. The device of the '357 patent implements a plurality of data acquisition circuits, typically five, to acquire data at high speed from an analog signal with or without data averaging. Each data acquisition circuit includes all hardware necessary to perform an analog-to-digital conversion, average the digital signal data, and temporarily store the averaged digital signal data prior to transfer to long-term storage. Essentially, the '357 device is a series of independent data acquisition systems operating in parallel. Because each data acquisition circuit employs a single, circular buffer, each memory undergoes one read and one write cycle during each summation limiting the computational speed. Furthermore, the '357 device experiences dead time during measurements because the ADC is disabled while the final summation is read from the memory.

In addition, the '357 device utilizes a lookup table for summing averaged data. The '357 device divides each potential output of the ADC by the number of samples to be taken and stores the quotient in the lookup table. As each sample produces an ADC output, the corresponding quotient in the lookup table is summed to create the averaged signal data.

Because the input sampling rate of the ADC is approximately forty-two times greater than the output transfer rate of each data acquisition circuit of the of the '357 device, non-averaged digital signal data is cached in burst memory. Accordingly, test time is limited by the size of the burst memory. In the '357 device, non-averaging testing times are limited to approximately two seconds.

Finally, when averaging data, sufficient averages must be taken to reduce the effective input rate to a level less than or equal to the output transfer rate for the chosen number of data acquisition circuits.

The U.S. Pat. No. 4,490,806 patent discloses a high repetition rate transient recorder with automatic integration with a maximum sampling rate limited by the maximum rate of available state-of-the-art ADC's. Further the '806 device is limited by the memory architecture which requires an even number of records to be summed, as explained in the following summary of the memory system of '806 device. The '806 device includes three pairs, A, B, and C, of summation devices and memory units for summing and storing digital signal data which is linearly acquired at a constant period. Summation/memory pairs A and C are configured to alternatively work with summation/memory pair B to sum the data for one spectrum. Furthermore, summation/memory pairs A and C are configured to transfer final summation to a permanent storage. In operation, analog data is received from a C/TOF-MS and converted to a digital representation by an ADC. The summation/memory pairs then sum and store the digital records to compile a spectrum, which contains the data from one set of records. The first record of a spectrum is always processed by summation/memory pair B. Within a spectrum, processing of each successive record alternates between either of summation/memory pair A or C and summation/memory pair B. This allows the memory read/write time to be halved by alternatively reading the previous sum from one memory, adding the previous sum to the newly acquired data, and writing the new sum to a second memory. For example, during the second record, the data from the first record is read from summation/memory pair B, summed with the newly acquired data, and the sum stored in summation/memory pair A. During the next record, the sum is stored in summation/memory pair B. This sequence alternates until the required number of records have been summed to form the spectrum. Because the first record is processed by summation/memory pair B and only summation/memory pairs A and C are equipped for output to permanent storage, an even number of records must be acquired for each spectrum so that the final summation is stored in summation memory pair A or C. At the conclusion of each spectrum acquisition, the output is transferred to permanent storage from the output summation/memory pair active during the spectrum acquisition while the other output summation/memory pair works in conjunction to process incoming data. Accordingly, the '806 device is limited to measuring an even number of records, which is undesirable in many applications.

Unfortunately, a C/TOF-MS instrument can produce data at a rate beyond the ability of conventional electronic instruments to analyze. For example, a single molecular type from the sample might be eluted from the chromatography device apparatus as a "surge" of two to five seconds duration which must be sampled in 100 millisecond intervals. The time per record of the TOF-MS system might be 100 microseconds. To obtain all the information available, the summation of one thousand records (100 msec/100 $\mu$sec) of the TOF-MS system would be required. The data in each record is obtained by sampling the TOF-MS output by the ADC. Because the fragment peaks in the mass spectrum may be only two nanoseconds wide and several samples are required over each peak, the sampling resolution of the ADC should be at least one sample per 0.5 nanosecond.

For each record, the data is summed with data from previously summed records. The instant example requires that the summing cycle be completed in less than 0.5 nanoseconds for each data point. Because ions arrive continuously, attempts to complete summing during dead time at the end of a pass would result in unacceptable data loss. Further, each pass produces 200,000 data points (100 $\mu$sec/0.5 $\mu$sec/data point) at the sampling interval of the ADC. After averaging, the resolution of the data increases to a size of eighteen to twenty-four bits, depending upon the ADC resolution. Transfer of all data points to long-term, memory must occur at the conclusion of each chromatograph sampling interval so that a new spectrum can be acquired. For a spectrum having a three-byte data size, approximately 600,000 bytes of data would have to be transferred while incurring less than one millisecond of dead time to achieve less than one percent data loss. One skilled in the art will recognize that readily-available, conventional hardware is not capable of data transfer at this rate.

Furthermore, one skilled in the art will recognize that digital sampling oscilloscopes (DSOs) and fast flash ADC systems solve similar problems in less demanding applications but cannot handle the unique requirements of the C/TOF-MS. By incorporating a variable delay between the trigger and the sampling point, high-speed DSOs achieve high bandwidth with fine time resolution. Each sample can be taken at a small offset relative to the previous sample, however, only one sample is taken for each scan, resulting in low throughput. Accordingly, a large number of scans are required to achieve one complete data record. This implementation is effective for oscilloscopes, but not for data averaging, because the method is prohibitively slow when extensive averaging is required.

Fast flash systems, such as interleaved flash ADCs, incorporate multiple high-speed ADCs operating in parallel. Each sample is processed by a different ADC allowing for a fine time resolution. However, the multiple ADC architecture results in d.c. gain and offset problems which are complicated and expensive to solve when attempting to relate ADC outputs. Furthermore, fast flash systems are not capable of sustained averaging and, therefore, experience significant sampling dead time while samples are being processed. Finally, the large amount of hardware required in fast flash systems is cost prohibitive.

Presently available C/TOF-MS instruments therefore suffer from three practical limitations making them unsuitable for many applications. First, an ADC with an inherent sample rate of at least 2 GHz (0.5 nsec sampling interval) is not presently practical. Second, completing the summing cycle for each data point in less than 0.5 nanoseconds exceeds the capability of any cost-effective, state-of-the-art averaging device. Finally, a data transfer channel with sufficient bandwidth to transfer a mass spectrum to long-term storage without data loss is impracticable.

While both the '806 and the '357 devices process acquired data in parallel, neither device contemplates increasing the effective sampling rate of a conventional ADC. Specifically, the '806 device linearly acquires digital signal data at a fixed phase with respect to the trigger and does not contemplate the use of multiple phase-shifted clock pulses to acquire data in successive phases for later reconstruction. Likewise, the '357 device linearly acquires data at a fixed phase with respect to the trigger.

Accordingly, it is an object of the present invention to provide a high-performance digital signal averager uniquely adapted to an apparatus combining gas, liquid, or capillary electrophoresis chromatography with a time-of-flight mass spectrometer.

Another object is to provide such a digital signal averager capable of meeting the rapid ADC sampling requirements of a C/TOF-MS instrument.

It is a further object of the present invention is to provide such a digital signal averager capable of sustained data processing cycles at high rates without significant data loss.

A still further object of the present invention is to provide such a digital signal averager capable of transferring mass spectrum data to long-term storage at high data transfer rates without data loss.

Yet another object of the present invention is to provide a memory architecture capable of acquiring any number, even or odd, of records in order to overcome deficiencies in the referenced prior art.

Other objects and advantages over the prior art will become apparent to those skilled in the art upon reading the detailed description together with the drawings as described as follows.

DISCLOSURE OF THE INVENTION

A digital signal averager for averaging data collected by an analog detector is provided. Specifically, the digital signal averager provides for a high effective sampling rate at a reasonable clock rate. Further the digital signal averager is particularly well-suited for averaging as it incurs little to no data loss. Finally, the high performance digital signal averager incorporates data compression to reduce the data transfer rate and storage capacity requirements.

One particular use of the present invention is with a conventional chromatograph time-of-flight mass spectrometer (C/TOF-MS). A timing device within the high performance digital signal averager generates a trigger which pulses the high voltage accelerator of the C/TOF-MS. Analog signal data collected by an analog detector of the C/TOF-MS is sampled by an analog-to-digital converter (ADC) at the sampling interval of the ADC. Because conventional, cost-effective ADCs are not capable of the small sampling intervals required, the start of the sampling sequence is offset from the trigger by a programmed delay generated by the timing device of the high performance digital signal averager, thus providing finer spacing of the sampling intervals than is offered by the basic ADC clock period.

In order to process the data acquired by the ADC in real time, a plurality of averaging devices operating in parallel is used. Each averaging device includes a processing device for summing the data and a plurality of memory units for storing the results. For example, three memory units can be used. Two memory units are used in ping-pong fashion for acquiring the sum. Data is read from a first memory, summed with the new ADC data, and the sum is written to a second memory. During the next record, data is read from the second memory, summed with the new ADC data, and the sum is written to the first memory. Upon acquiring the final record, the summed data is concurrently written to both the appropriate summing memory and to an output memory. The output memory holds the final sum for output to an analysis and storage device while the data acquisition process continues using the summing memories to acquire new data.

To further reduce the dead time incurred during data output, a digital signal processor is used to processes the spectra, employing a method for data compression to reduce the amount of data which must be transferred to the analysis and storage device, effectively reducing the data transfer rate and the storage capacity requirements.

BEST MODE FOR CARRYING OUT THE INVENTION

A high-performance digital signal averager, uniquely adapted for use in conjunction with a combined gas, liquid, or capillary electrophoresis chromatography and time-of-flight mass spectrometry (C/TOF-MS) apparatus, constructed in accordance with the present invention, is illustrated generally as 10 in the figures.

Figure 1:
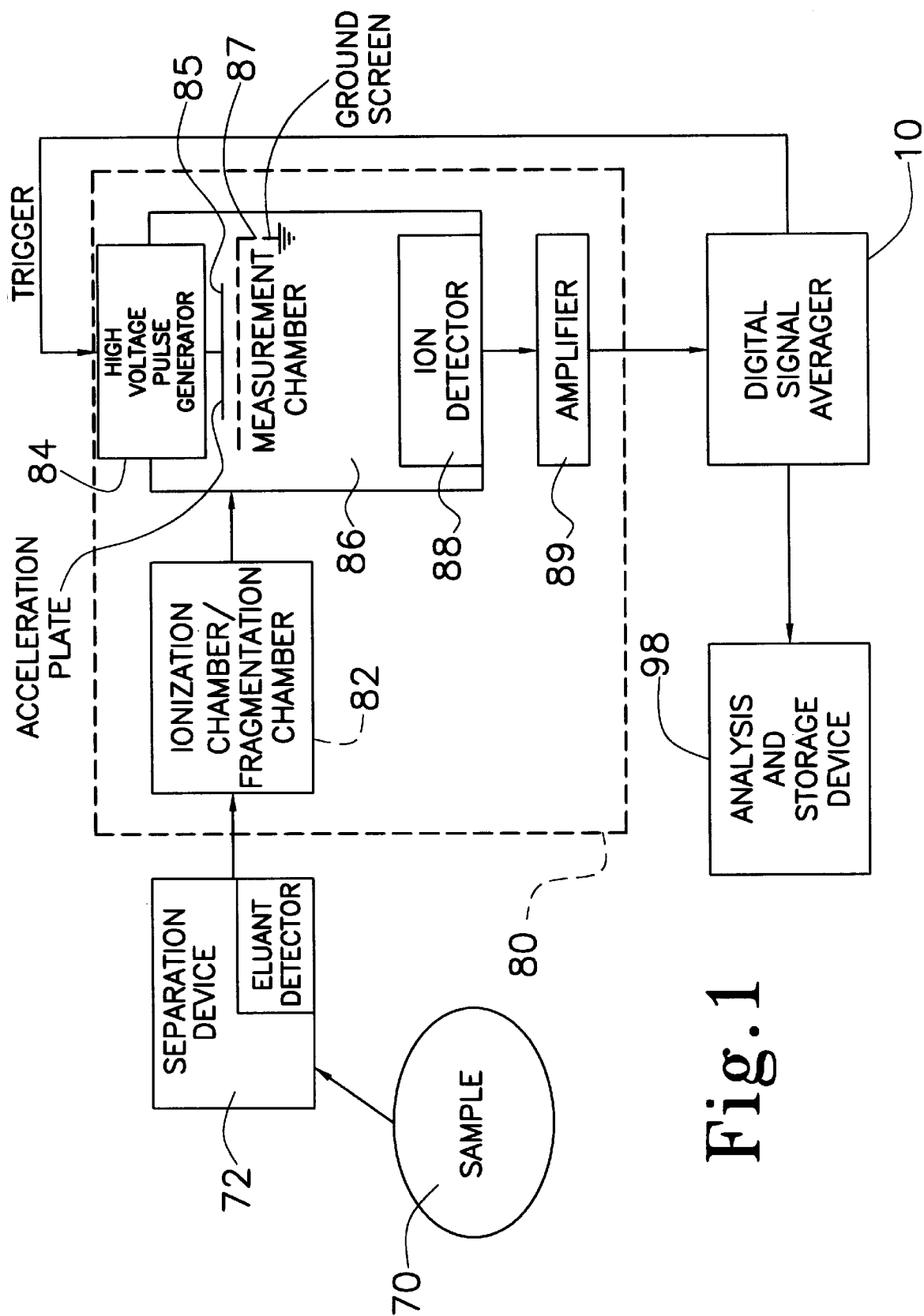
FIG. 1 illustrates a schematic view of a combined gas, liquid, or capillary electrophoresis chromatograph and time-of-flight mass spectrometry instrument incorporating the high performance digital signal analyzer.

FIG. 1 illustrates a C/TOF-MS apparatus incorporating a high-performance digital signal averager 10. A molecular sample 70 is introduced into a separation device 72, such as a chromatograph, for separating the molecular sample 70 into its component molecules. Those skilled in the art will recognize that the separation device 72 is any conventional device such as one that employs gas, liquid, or capillary electrophoresis chromatography. The separation device output is fed directly into a time-of-flight mass spectrometry device (TOF-MS) 80. One skilled in the art will recognize that some ionization techniques include fragmentation. Depending upon the voltage applied in the ionization and fragmentation chamber 82, the molecules are either ionized or ionized and fragmented and then accelerated through a measurement chamber 86 toward an ion detector 88 by a pulsed, high-voltage accelerator 84 having an acceleration plate 85 and a ground screen 87. When ions having a specific mass-to-charge ratio have traversed the measurement chamber 86, their arrival at the detector 88 is recorded as a voltage, the average of which is proportional to the number of ions striking the ion detector 88. An amplifier 89 conditions the output of the ion detector 88 prior to processing by the digital signal averager 10. The processed data is transferred to an analysis and storage device 98 for study and long term storage.

Figure 2:
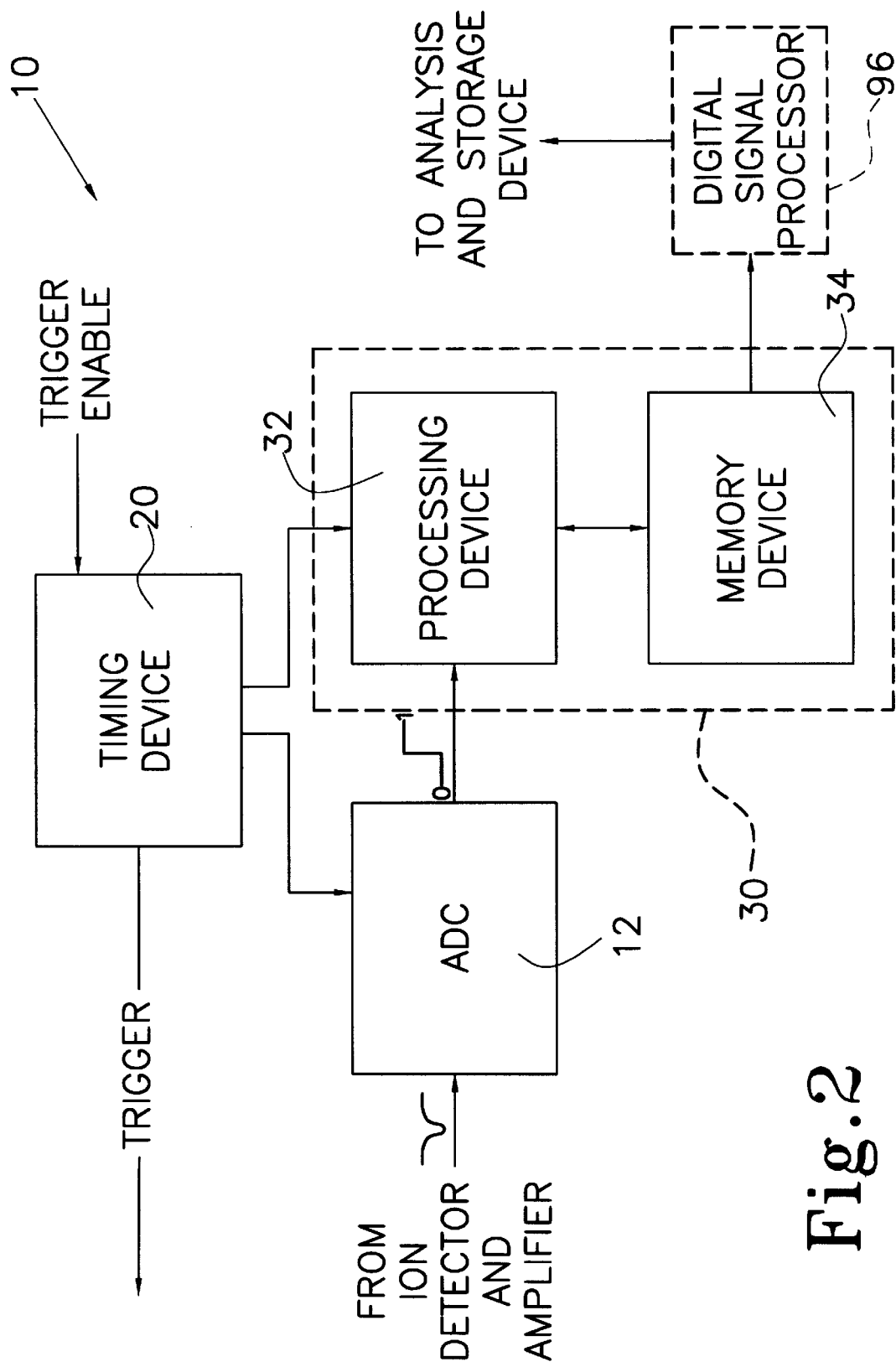
FIG. 2 illustrates a schematic view of the high performance digital signal analyzer.

Referring now to FIG. 2, the digital signal averager 10 includes an analog-to-digital converter (ADC) 12, a timing device 20, and at least one averaging device 30. The averaging device 30 includes a processing device 32 for receiving the digital output of the ADC 12 and a memory device 34 for temporary storage of data during processing. Data from memory 34 is transferred to analysis and storage device 98 at the end of each chromatograph sampling interval. Furthermore, one skilled in the art will recognize that modifications such as the addition of a digital signal processor 96 for data compression or other processing can be added to the output path. Various data compression methods may be employed, such as lossless data compression methods described by Nelson, Mark; Jean-Loup Gailly, *The Data Compression Book*, M&T Books, New York, 1995. Additionally, a method may be employed that adaptively filters useless baseline data and preserve useful data which in a typical application is in the neighborhood of peaks in the spectrum. One skilled in the art will recognize that other data compression methods may be successfully employed.

Figure 3:
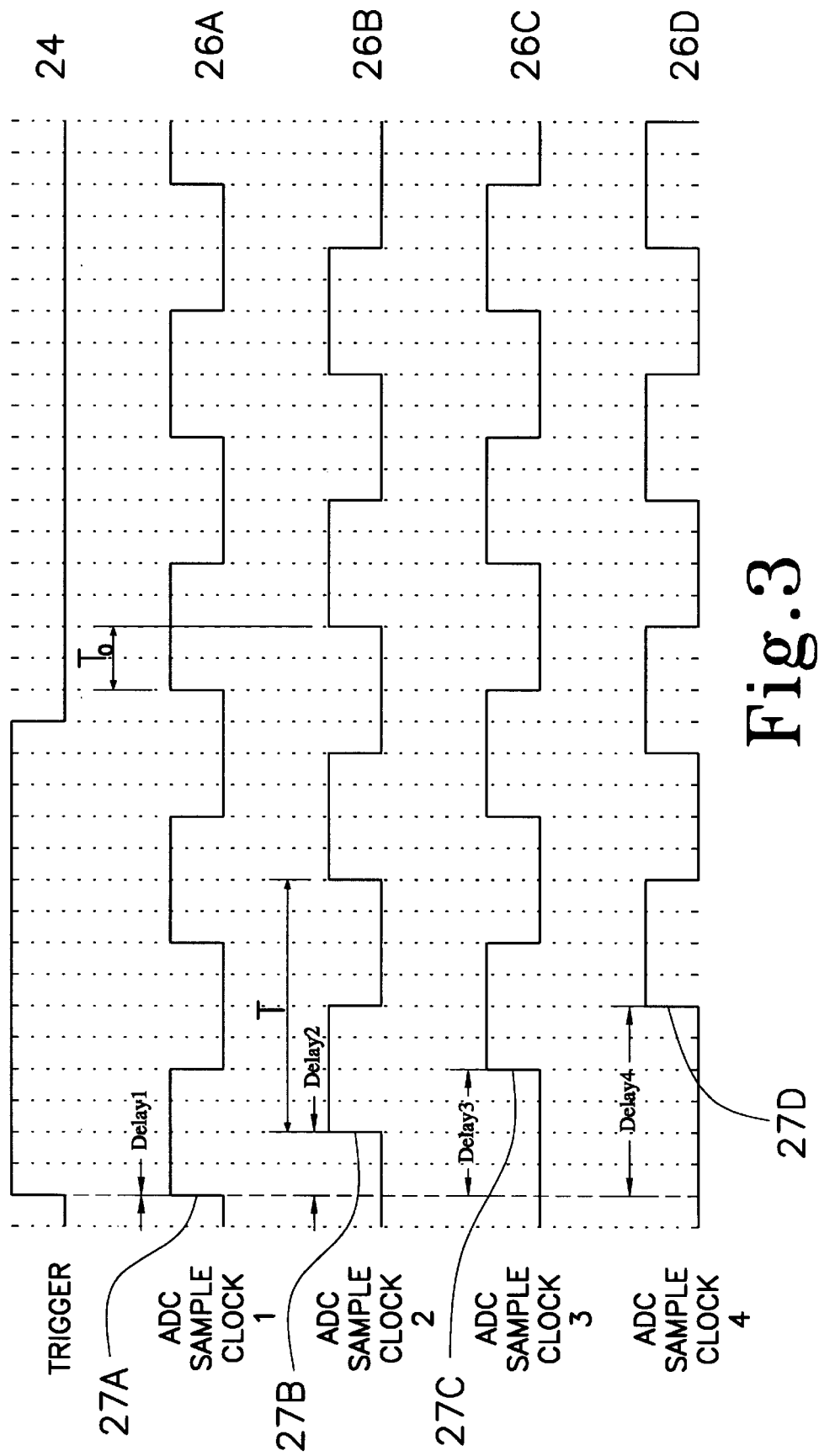
FIG. 3 illustrates a representation of the trigger signal and four phase-shifted timing signals used in the present invention.

In the illustrated embodiment of FIG. 3, the timing device 20 generates a clock pulse 26 and a trigger pulse 24 with a variable delay for sequencing the operation of the digital signal averager 10. One skilled in the art will recognize that the same result is achieved by either delaying the clock 26 with respect to the trigger 24 or delaying the trigger with respect to the clock 26. By varying the delay between the trigger pulse 24 and the clock pulse 26, the output of the ion detector 88 can be sampled at various times with respect to the accelerating pulse from the pulsed high-voltage accelerator 84, thus providing finer spacing of the sampling intervals than is offered by the basic ADC clock period. One skilled in the art will recognize that the number of differing delays used depends upon the speed of a conventional ADC relative to the desired "effective" sampling rate.

In the illustrated embodiment, a clock 26 having period, T, is delayed relative to the trigger 24. On successive scans, the delay between the trigger 24 and the first clock pulse 26 of the scan is increased by T divided by the number of delays, N, used. The illustrated embodiment uses a two nanosecond clock period and a series of four delays to achieve an effective sampling rate of 0.5 $\mu$sec/sample, however, one skilled in the art will recognize that any number of delays could be used to achieve a desired "effective" sampling rate. One skilled in the art will recognize that a variety of methods may be employed to generate the desired delays including, but not limited to, using analog delay lines and counting down a clock whose period is equal to the size of the delay step.

On the edge 27 of each clock pulse 26 from timing device 20, the ADC 12 samples and converts the analog output of the ion detector 88 to a digital signal for processing. Cycling through the addresses of the memory device 34, the processing device 32 reads the contents of the memory device 34 at the current memory address, adds the digital output of the ADC 12 to the read data, and writes the summed data to the memory device 34. At the end of each scan, the variable delay is incremented and the beginning memory address for the memory address cycle is set to an address corresponding to the current variable delay. At the conclusion of the chromatograph sampling interval, the summed data is transferred to the analysis and storage device 98.

Figure 4:
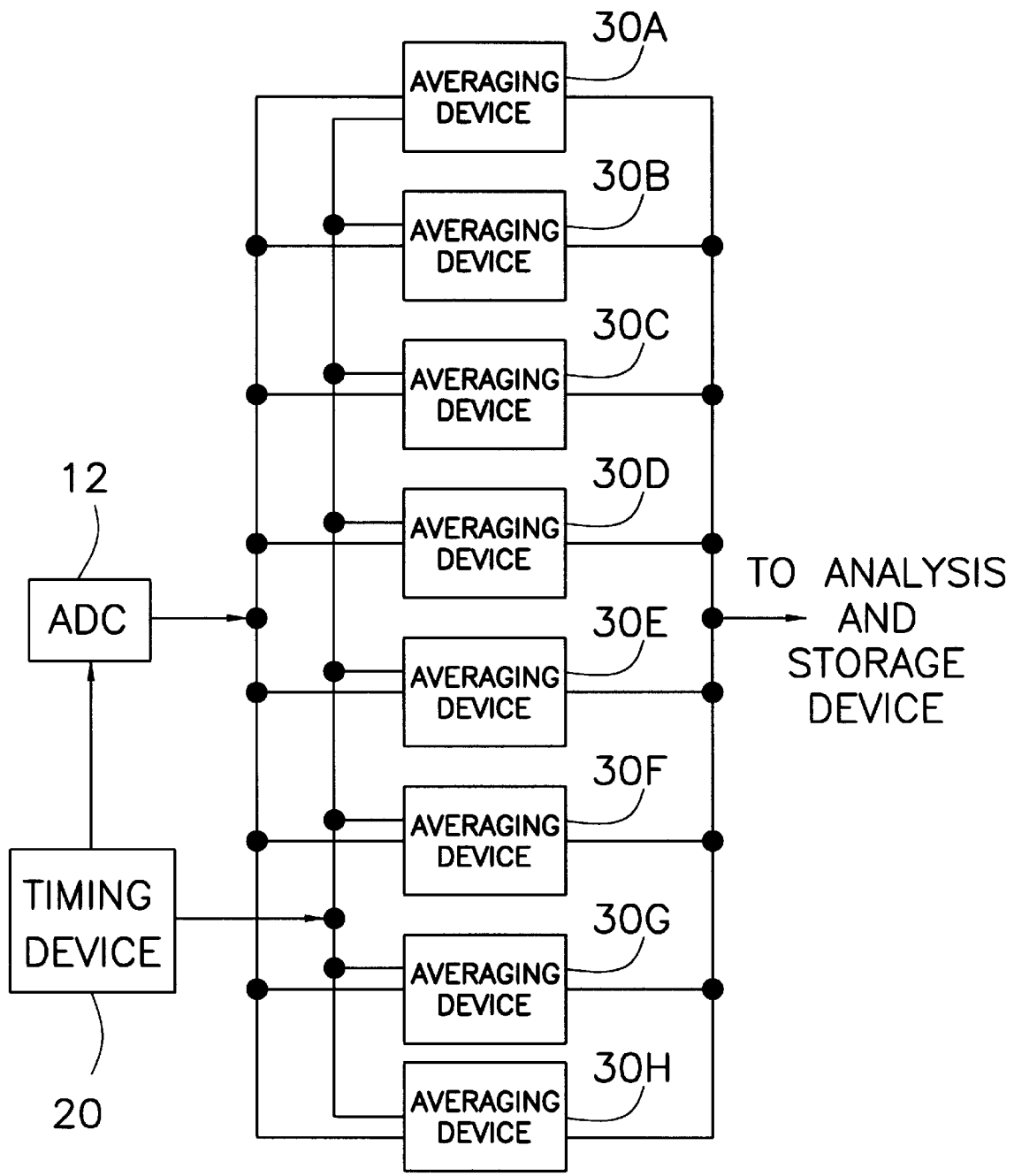
FIG. 4 illustrates a schematic view of the high performance digital signal averager showing the parallel processing-memory architecture of the present invention.

In order to obtain high data throughput without incurring excessive data processing delays, the digital signal averager 10 includes multiple averaging devices 30, operating in parallel. The digital signal averager 10 incorporating eight averaging devices 30 operating in parallel is illustrated in FIG. 4. One skilled in the art will recognize that, while any number of averaging devices 30 can be used, the minimum number of averaging devices 30 necessary to process and store all data available from the ADC 12 is generally determined by dividing the total processing/storage time for the averaging device 30 by the period, T, between two successive clock pulses.

One skilled in the art will recognize that the type and number of components comprising the memory device 34 vary with the desired acquisition rate and the current state-of-the-art of the available memory devices. One such implementation, illustrated in FIG. 5, uses currently available memory devices designed for rapid block-data transfer, for example synchronous burst-mode RAM (SBRAM). SBRAM is optimized for the rapid transfer of large blocks of data, however, this optimization hinders switching between reads and writes. The illustrated embodiment includes at least one data memory device 36 and a transfer memory device 38.

Each averaging device 30, in rotation, receives the current digital output of the ADC 12 for processing. To overcome the mode switching limitation of SBRAM, each averaging device 30 of the illustrated embodiment includes two identically-addressed, data memory devices 36: a first data memory device 36A and a second data memory device 36B. On odd numbered records, the processing device reads data from the first data memory device 36A, sums the read data with the digital signal from the ADC 12, and writes the sum to the second data memory device 36B. Conversely, on even-numbered records, the processing device reads data from the second data memory device 36B, sums the read data with the digital signal from the ADC 12, and writes the sum to the first data memory device 36A. One skilled in the art will recognize that the implementation of memory storage varies with the type, number, and speed of the components of the memory device selected for the application.

A complete set of data taken at the desired effective sampling rate, termed a "record," can be recorded in N scans. With each of the N scans, information is obtained at a finer time resolution. A finer time resolution provides more detailed information on peak shapes allowing more accurate decovolution of overlapping peaks in the mass spectrum. Averaging multiple records, each comprising N scans further improves measurements by reducing the effect of statistical variations in the signal.

It is informative to compare the results of an $ADC_A$ sampling at a period, T, without delay steps to an $ADC_B$ sampling at a period, T, employing N delay steps of size T/N. $ADC_B$ must perform N scans to produce a signal record. In the time it takes $ADC_B$ to acquire one record, $ADC_A$ can sum N records. However the number of data points in a record from $ADC_B$ will be N times the number of data points in a record from $ADC_A$. The data points from $ADC_A$ are spaced at intervals equal to T, whereas the data points from $ADC_B$ are spaced at intervals equal to T/N. If a mass spectrum is acquired from one record with $ADC_B$ and for N records with $ADC_A$ (i.e. equal measurement times) the areas of the peaks in both spectra will be identical. But, the area will be spread over a factor of N more data points for $ADC_B$ thus better defining the shape of each peak.

At the end of each chromatograph sampling interval, the acquired mass spectrum must be transferred from the memory device 34 to an analysis and storage device 98. In the illustrated embodiment, the analysis and storage device 98 is a conventional microcomputer. To minimize data loss, transfer time should be less than one percent of the length of the chromatograph sampling interval. In the illustrated embodiment, the processing device 32 simultaneously writes the summed data to the transfer memory device 38 and the data memory device 36 during the final record of a chromatograph sampling interval. The analysis and storage device 98 reads the data from the transfer memory device 38 during the following chromatograph sampling interval. Accordingly, the transfer memory device 38 undergoes only one write cycle per chromatograph sampling interval, thereby reducing the speed requirements for data transfer.

Figure 5:
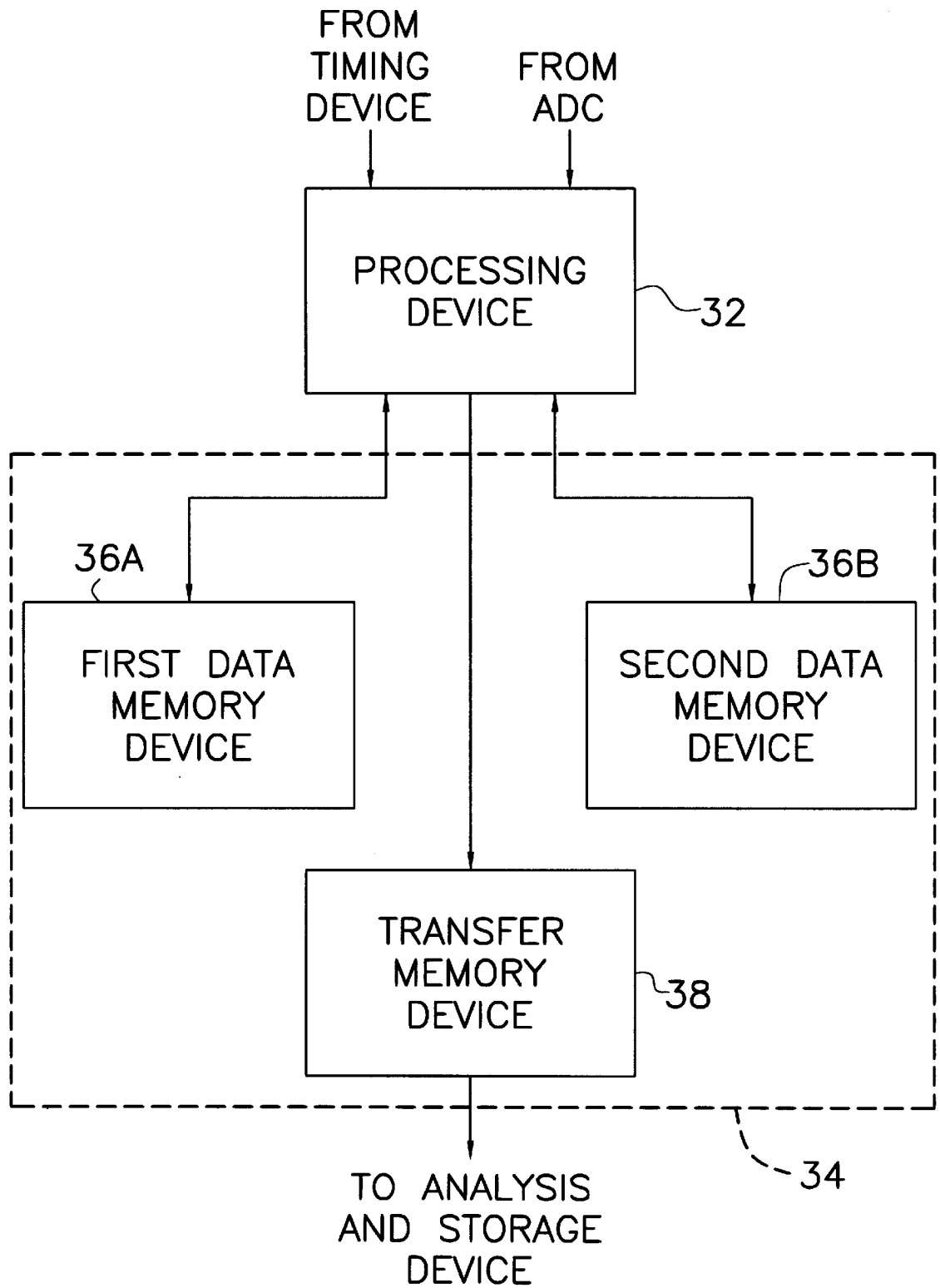
FIG. 5 illustrates a schematic view of the averaging device of the present invention.

With the embodiment illustrated in FIG. 5 either even or odd numbers of records can be accommodated in each chromatograph sampling interval without stopping data acquisition for the purpose of transferring previously acquired data to the analysis and storage device 98.

Furthermore, the DSP 96 processes the spectra, employing a method for data compression to reduce the amount of data which must be transferred to the analysis and storage device 98. The data compression effectively reduces the data transfer rate and the storage capacity requirements.

While the foregoing specification describes the digital signal averager in conjunction with a C/TOF-MS instrument, one skilled in the art will recognize that the high performance digital signal averager 10 can be used in conjunction with an analog detector output from other instruments.

From the foregoing description, it will be recognized by those skilled in the art that a high-performance digital signal averager offering advantages over the prior art has been provided. Specifically, the high-performance digital signal averager provides a device for acquiring rapidly accumulating data from a mass spectrometer with improved effective sampling rates and with little data loss using conventional, cost-effective hardware.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention.

We claim:

1. A digital signal averager for averaging data acquired from an analog detector at high speed and transferring averaged data to an analysis and storage device, said digital signal averager comprising:

an analog-to-digital converter for converting the output of an analog detector to a digital signal data for processing, said analog-to-digital converter having an actual sampling rate;

a timing device for generating a plurality of delayed timing pulses for sequencing operation of said digital signal averager during at least one record in order to achieve an effective sampling rate higher than said actual sampling rate, said at least one record comprised of a plurality of scans of said analog-to-digital converter sequenced on said plurality of delayed timing pulses for acquiring said digital signal data, said plurality of delayed timing pulses comprising at least one trigger pulse and a plurality of clock pulses and including at least one time delay; and an averaging device for sustained averaging of said digital signal data at said actual sampling rate of said analog-to-digital converter, said averaging device comprising at least one processing device for summing said digital signal data and at least one memory device for storing said digital signal data and for output of a spectrum, said spectrum comprising an average of said at least one record.

2. The digital signal averager of claim 1 wherein said plurality of clock pulses is temporally delayed from said at least one trigger pulse by one of a plurality of delays.

3. The digital signal averager of claim 1 wherein said at least one trigger pulse is temporally delayed from said at least one clock pulse by one of a plurality of delays.

4. The digital signal averager of claim 1 wherein said delayed timing pulses sequence collection of said digital signal data from each successive said plurality of scans such that said at least one record includes said digital signal data acquired at said effective sampling rate.

5. The digital signal averager of claim 1 wherein said digital signal averager includes a digital signal processor employing a method for data compression applied to said spectrum.

6. The digital signal averager of claim 1 wherein said at least one memory device includes a plurality of memory units operating in parallel such that a sum of digital signal data is read from one of said plurality of memory units, processed by said at least one averaging device, and written to another of said plurality of memory units.

7. The digital signal averager of claim 6 wherein said plurality of memory units includes three memory units including two sum memories, and an output memory, wherein, on successive said records, a sum of said digital signal data is alternatively read from a first sum memory, processed by said at least one averaging device, and written to a second sum memory, and read from said second sum memory, processed by said at least one averaging device, and written to said first sum memory, wherein upon acquisition of a final said record, the sum of said digital signal data is concurrently written to one of said sum memories and to said output memory, said output memory storing the sum of said digital signal data for output to an external device while said sum memories accumulate a new sum of digital signal data.

8. A digital signal averager for averaging data acquired from an analog detector at high speed and transferring averaged data to an analysis and storage device, said digital signal averager comprising:

an analog-to-digital converter for converting the output of an analog detector to a digital signal data for processing, said analog-to-digital converter having an actual sampling rate;

a timing device for generating a plurality of delayed timing pulses for sequencing operation of said digital signal averager during at least one record in order to achieve an effective sampling rate higher than said actual sampling rate, said delayed timing pulses sequence collection of said digital signal data from each successive said plurality of scans such that said at least one record includes said digital signal data acquired at said effective sampling rate, said at least one record comprised of a plurality of scans of said analog-to-digital converter sequenced on said plurality of delayed timing pulses for acquiring said digital signal data, said plurality of delayed timing pulses comprising at least one trigger pulse and a plurality of clock pulses and including at least one time delay, said plurality of clock pulses being temporally delayed from said at least one trigger pulse by one of a plurality of delays or said at least one trigger pulse being temporally delayed from said at least one clock pulse by one of a plurality of delays; and an averaging device for sustained averaging of said digital signal data at said actual sampling rate of said analog-to-digital converter, said averaging device comprising at least one processing device for summing said digital signal data and at least one memory device for storing said digital signal data and for output of a spectrum, said spectrum comprising an average of said at least one record.

9. The digital signal averager of claim 8 wherein said digital signal averager includes a digital signal processor employing a method for data compression applied to said spectrum.

10. The digital signal averager of claim 8 wherein said at least one memory device includes a plurality of memory units operating in parallel such that a sum of digital signal data is read from one of said plurality of memory units, processed by said at least one averaging device, and written to another of said plurality of memory units.

11. The digital signal averager of claim 10 wherein said plurality of memory units includes three memory units including two sum memories, and an output memory, wherein, on successive said records, a sum of said digital signal data is alternatively read from a first sum memory, processed by said at least one averaging device, and written to a second sum memory, and read from said second sum memory, processed by said at least one averaging device, and written to said first sum memory, wherein upon acquisition of a final said record, the sum of said digital signal data is concurrently written to one of said sum memories and to said output memory, said output memory storing the sum of said digital signal data for output to an external device while said sum memories accumulate a new sum of digital signal data.

12. A digital signal averager for averaging data acquired from an analog detector at high speed and transferring averaged data to an analysis and storage device, said digital signal averager comprising:

an analog-to-digital converter for converting the output of an analog detector to a digital signal data for processing, said analog-to-digital converter having an actual sampling rate;

a timing device for generating a plurality of delayed timing pulses for sequencing operation of said digital signal averager during at least one record in order to achieve an effective sampling rate higher than said actual sampling rate, said delayed timing pulses sequence collection of said digital signal data from each successive said plurality of scans such that said at least one record includes said digital signal data acquired at said effective sampling rate, said at least one record comprised of a plurality of scans of said analog-to-digital converter sequenced on said plurality of delayed timing pulses for acquiring said digital signal data, said plurality of delayed timing pulses comprising at least one trigger pulse and a plurality of clock pulses and including at least one time delay, said plurality of clock pulses being temporally delayed from said at least one trigger pulse by one of a plurality of delays or said at least one trigger pulse being temporally delayed from said at least one clock pulse by one of a plurality of delays;

an averaging device for sustained averaging of said digital signal data at said actual sampling rate of said analog-to-digital converter, said averaging device comprising at least one processing device for summing said digital signal data and at least one memory device for storing said digital signal data and for output of a spectrum, said spectrum comprising an average of said at least one record, at least one memory device includes three memory units including two sum memories, and an output memory, wherein, on successive said records, a sum of said digital signal data is alternatively read from a first sum memory, processed by said at least one averaging device, and written to a second sum memory, and read from said second sum memory, processed by said at least one averaging device, and written to said first sum memory, wherein upon acquisition of a final said record, the sum of said digital signal data is concurrently written to one of said sum memories and to said output memory, said output memory storing the sum of said digital signal data for output to an external device while said sum memories accumulate a new sum of digital signal data; and a digital signal processor for compressing said digital signal data.

\* \* \* \* \*

UNITED STATES PATENT AND TRADEMARK OFFICE
CERTIFICATE OF CORRECTION

PATENT NO.    : 6,094,627
DATED         : July 25, 2000
INVENTOR(S)   : Peck et al.

It is certified that error appears in the above-identified patent and that said Letters Patent is hereby corrected as shown below:

Column 7,
Line 7, delete "preserve" and insert -- preserves --.
Line 33, delete "$\mu$/sec" and insert -- n/sec --.

Column 9,
Line 38, delete "to a digital signal" and insert -- to digital signal --.

Column 10,
Line 33, delete "to a digital signal" and insert -- to digital signal --.

Signed and Sealed this

Twenty-third Day of July, 2002

Attest:

JAMES E. ROGAN
Attesting Officer          Director of the United States Patent and Trademark Office